(12) United States Patent
Ha

(10) Patent No.: US 11,471,705 B2
(45) Date of Patent: Oct. 18, 2022

(54) HIFU SKIN CARE DEVICE AND CARTRIDGE

(71) Applicant: Medicon Co., Ltd., Wonju-si (KR)

(72) Inventor: Dong Hoon Ha, Wonju-si (KR)

(73) Assignee: Medicon Co., Ltd., Wonju-si (KR)

( * ) Notice: Subject to any disclaimer, the term of this patent is extended or adjusted under 35 U.S.C. 154(b) by 0 days.

(21) Appl. No.: 16/632,238

(22) PCT Filed: Nov. 15, 2018

(86) PCT No.: PCT/KR2018/013952
§ 371 (c)(1),
(2) Date: Apr. 16, 2020

(87) PCT Pub. No.: WO2020/075906
PCT Pub. Date: Apr. 16, 2020

(65) Prior Publication Data
US 2021/0220677 A1    Jul. 22, 2021

(30) Foreign Application Priority Data

Oct. 11, 2018 (KR) ......................... 10-2018-0121309
Oct. 17, 2018 (KR) ......................... 10-2018-0123868

(51) Int. Cl.
*A61N 7/02* (2006.01)
*A61L 2/00* (2006.01)
(Continued)

(52) U.S. Cl.
CPC .............. *A61N 7/02* (2013.01); *A61L 2/0047* (2013.01); *A61L 2/26* (2013.01); *A61L 2202/11* (2013.01);
(Continued)

(58) Field of Classification Search
CPC . A61N 7/02; A61N 2007/0034; A61L 2/0047; A61L 2/26; A61L 2202/11; H02J 7/0044
See application file for complete search history.

(56) References Cited

FOREIGN PATENT DOCUMENTS

JP          2012-71041 A     4/2012
KR    10-2017-0027263 A     3/2017
(Continued)

OTHER PUBLICATIONS

Imternational Search Report and Written Opinion received for PCT/KR2018/013965, dated Jul. 8, 2019, 12 pgs.

*Primary Examiner* — Nicole M Ippolito
*Assistant Examiner* — Hanway Chang
(74) *Attorney, Agent, or Firm* — Michael Bondi; Moss & Barnett

(57) ABSTRACT

The present invention relates to a portable HIFU skin care device. The portable HIFU skin care device (1) of the present invention is divided into three portions. Firstly, a main body (100) has a rechargeable battery embedded therein, a power button and a step button installed therein for adjusting the intensity of an ultrasonic wave, and a display for displaying the operation states of the device, including the number of shots. In addition, a cartridge (200) is used by being mounted on a head part of the main body (100) and has a HIFU transducer embedded therein. A cradle (300) has a charging part which is installed therein, is capable of charging by being connected with the cartridge (200) and an adaptor, accommodates the main body (100) through a placement groove while the cartridge (200) is mounted to the main body (100), includes a UV lamp for disinfecting the head part of the cartridge (200) when accommodating the main body (100), and charges an internal battery of the main body (100). In an operation state, while the HIFU transducer is linearly moved for each one shot by a piezoelectric motor, a plurality of ultrasonic waves are emitted so as to form a (Continued)

plurality of ultrasonic focal point regions on an object, thereby achieving a skin care effect. In the present invention, the piezoelectric motor (216) is particularly installed inside the cartridge (200).

13 Claims, 12 Drawing Sheets

(51) Int. Cl.
 *A61L 2/26* (2006.01)
 *A61N 7/00* (2006.01)
 *H02J 7/00* (2006.01)
(52) U.S. Cl.
 CPC ..... *A61N 2007/0034* (2013.01); *H02J 7/0044* (2013.01)

(56) References Cited

FOREIGN PATENT DOCUMENTS

| | | | |
|---|---|---|---|
| KR | 10-2017-0085018 A | 7/2017 |
| KR | 10-2017-0095550 A | 8/2017 |
| KR | 10-2017-0100420 A | 9/2017 |

(a)

(b)　　　(c)　　　(d)

(e)

(a)

(b)

(c)

HIFU SKIN CARE DEVICE AND CARTRIDGE

TECHNICAL FIELD

The present invention relates to a skin care device using an ultrasonic wave, and particularly, to a device-related technique for achieving skin care and therapeutic-purpose treatment by using a high-intensity focused ultrasonic (HIFU) wave.

BACKGROUND ART

HIFU devices have characteristics of directly applying heat to a human body using a strongly focused ultrasonic wave. The HIFU devices according to related arts are known as equipment for treating cancers such as a liver cancer, a uterine cancer, and a breast cancer, by focusing an ultrasonic wave having a high intensity (focused region strength of at least 1000 $W/cm^2$) to a single focal point and by the necrosis or ablation of tumor tissues. The treatment method using HIFU equipment is a noninvasive method and is recognized to have a higher speed of patient recovery and to be safer than a surgical method, and therefore tends to have increasing demand.

Ultrasonic waves are not harmful when passing through human tissues, but a high-intensity ultrasonic wave that forms a focal point generates energy sufficient to cause necrosis regardless of the types of tissues. In a HIFU device, it is important to focus high-intensity energy to a target focal point of a body through a linear/rotary movement of an ultrasonic wave transducer that converts electrical energy into mechanical vibration energy within an ultrasonic frequency range, and thus, an accurate motion control of the transducer is required. The focal distance, the positional accuracy of the focal point, the irradiation time, and the temperature within a focal region are also important factors. In addition, the research and technology on these factors have advanced remarkably.

Such HIFU technology has been variously applied. The technology is being used not only for the purpose of treating tumor tissues, but also for the purpose of skin care, such as winkle treatment, and the purpose of treating obesity. For example, patent document 1 below discloses a HIFU treatment hand piece used by being connected to an equipment body.

However, the HIFU treatment hand piece of patent document 1 below is used by being connected to high-price equipment used in hospitals, and has a problem of being portably unusable because the power for applying a high-intensity ultrasonic wave to the skin of a subject to be treated is supplied from the equipment body. Accordingly, an operator inevitably undergoes inconvenience to come to a hospital having such equipment.

In addition, the HIFU treatment hand piece has a disadvantage of having a structure of driving a transducer inside a cartridge by means of a motor installed outside the cartridge, having larger power consumption, and having difficulty in establishing a heat dissipation measure due to heat generated due to the driving of the motor.

To address such problems, the inventors of the present invention arrive at the present invention after carrying out very long-term research and development.

PRIOR PATENT DOCUMENTS (Patent document 1) Korean Patent publication No. 10-2016-0144755

DISCLOSURE OF THE INVENTION

TECHNICAL PROBLEM

The purpose of the present invention is to provide a portable skin care device which may lift the skin (hereinafter, referred to as an "object") of a user and remove wrinkles of an object by using HIFU technology. An ultrasonic skin care device of the present invention is not an apparatus used by being connected to a 220 V commercial power supply (110 V etc. in case of Japan), but an apparatus usable for personal use, or usable in a skin care shop or a hospital. Therefore, the ultrasonic skin care device may be used by charging an internal battery and may be conveniently used by only a simple operation.

In addition, another purpose of the present invention is to provide a HIFU skin care device which guarantees accurate performance by completing a low-power mechanical mechanism regarding the driving of a transducer, not outside a cartridge (inside a main body), but inside the cartridge (outside the main body), and which maintains performance (rather improves performance) even when replacing the cartridge multiple times.

Still another purpose of the present invention is to provide a cartridge that is usable by being attached/detached to/from the HIFU skin care device. The skin care device at this point is not necessarily portable.

Meanwhile, other unspecified purposes of the present invention will be further considered within a scope that can be easily inferred from the detailed descriptions below and the effects thereof.

TECHNICAL SOLUTION

According to a first aspect of the present invention, a portable HIFU skin care device includes:

a main body (100) having a rechargeable battery embedded therein, a power button and a step button installed therein for adjusting the intensity of an ultrasonic wave, and a display for displaying operation states of the device, including the number of shots; a cartridge (200) used by being mounted on a head part of the main body (100) and having a HIFU transducer embedded therein; and a cradle (300) including a charging part installed therein and capable of charging by being connected with an adaptor, configured to accommodate the main body (100) via a placement groove while the cartridge (200) is attached to the main body (100), including a UV lamp for disinfecting the head portion of the cartridge (200) when the cradle accommodates the main body (100), and configured to charge an internal battery of the main body (100), wherein In an operation state, the HIFU transducer irradiates an object with a plurality of ultrasonic waves for each one shot while linearly moving by a piezoelectric motor installed inside the cartridge, and thereby forms a plurality of ultrasonic wave focal point regions on the object.

In the portable HIFU skin care device according to a preferred embodiment of the present invention, the HIFU transducer may move 1 mm ten times during one shot and may thereby form the focal point region of 10 mm.

In addition, according to a second aspect of the present invention, a portable HIFU skin care device includes:

a main body (100) having a rechargeable battery embedded therein, a power button and a step button installed therein for adjusting the intensity of an ultrasonic wave, and a display for displaying operation states of the device, including the number of shots; a cartridge (200) used by being mounted on a head part of the main body (100) and having a HIFU transducer embedded therein; and a cradle (300) including a charging part installed therein and capable of charging by being connected with an adaptor, and configured to accommodate the main body (100) via a placement groove and charge an internal battery of the main body (100) while the cartridge (200) is attached to the main body (100), wherein: three control units are installed inside the portable HIFU skin care device;

a first control unit and a second control unit are installed inside the main body (100) and a third control unit is installed to the cartridge (200);

the first control unit, which is a main control unit, controls a function of an input/output device of the portable HIFU skin care device, receives position data and skin contact presence/absence data about the piezoelectric motor from the third control unit, and transmits the data to the second control unit; the second control unit controls a motor driver and a HIFU driver which are required to drive the piezoelectric motor and the HIFU transducer that are installed inside the cartridge (200); and the third control unit performs an operation of transmitting, to the first control unit, the number of shots made by driving the motor driver and the HIFU driver of the second control unit.

In addition, according to a third aspect of the present invention, a portable HIFU skin care device includes:

a main body (100) having a rechargeable battery embedded therein, a power button and a step button installed therein for adjusting the intensity of an ultrasonic wave, and a display for displaying operation states of the device, including the number of shots; a cartridge (200) used by being mounted on a head part of the main body (100) and having a HIFU transducer embedded therein; and a cradle (300) including a charging part installed therein and capable of charging by being connected with an adaptor, and configured to accommodate the main body (100) via a placement groove and charge an internal battery of the main body (100) while the cartridge (200) is attached to the main body (100), wherein:

a PCB in which a control unit for the cartridge (200) is installed is installed on a rear surface protrusion part on an exterior of a cartridge housing, and when the PCB is mounted on the main body (100), a connector terminal part of the PCB and a connector installed on the head part of the main body (100) are electrically connected to each other;

a transducer moving mechanism including a piezoelectric motor is installed in a first chamber inside the cartridge (200);

The housing of the HIFU transducer is positioned inside a second chamber, which protrudes toward a front surface in a smaller width than the first chamber while communicating with the first chamber; and the protruding surface of the second chamber is configured as an action part brought into surface contact with the object.

In a portable HIFU skin care device according to a preferred embodiment of the present invention, the first chamber and the second chamber may communicate with each other and serve as a tank that accommodates distilled water.

In addition, in a portable HIFU skin care device according to a preferred embodiment of the present invention, a sealing member may further be installed to an entrance corresponding to the rear surface protrusion part of the first chamber.

In addition, in a portable HIFU skin care device according to a preferred embodiment of the present invention, a window through which a high-intensity ultrasonic wave is emitted may be installed in the middle of the action part.

According to a fourth aspect of the present invention, a cartridge which is for a HIFU skin care device, is used by being mounted on the head part of the main body, and is separable from the main body, is characterized in that:

a PCB, in which a control unit for the cartridge is installed, is installed to a rear surface protrusion part on the exterior of a housing of the cartridge, and when the PCB is installed to the main body, a connection terminal of the PCB and a connector installed on the head part of the main body are electrically connected to each other; an ultrasonic wave transducer moving mechanism device including a piezoelectric motor is installed in the first chamber inside the cartridge; a housing of the ultrasonic wave transducer is positioned inside a second chamber communicating with the first chamber and protruding toward a front surface in a smaller width than the first chamber; and an exterior protruding surface of the second chamber is configured as an action part brought into contact with an object.

In a cartridge for a HIFU skin care device according to a preferred embodiment of the present invention, the first chamber and the second chamber may serve as tanks that communicate with each other and stores distilled water, and a sealing member may further be installed to an entrance corresponding to the rear protruding part.

In a cartridge for a HIFU skin care device according to an embodiment of the present invention, a window, through which a high-intensity ultrasonic wave is emitted, may be installed in the middle of the action part.

In addition, in a cartridge for a HIFU skin care device according to a preferred embodiment of the present invention, the ultrasonic wave moving mechanism device may include a mover module coupled to the ultrasonic wave transducer, a carbon shaft connected to the piezoelectric motor may pass through a central hole of the mover installed to an upper end of the mover module, a mover fixation hole and a mover fixation guide, which are installed to a pair of respective mover pieces divided into two pieces with respect to the central hole, may be coupled to face each other; and the mover may be installed to the carbon shaft by inserting a mover fixation rubber into a recess part of the mover.

In addition, in a cartridge for a HIFU skin care device according to a preferred embodiment of the present invention, when the cartridge is mounted to the main body, a cartridge control unit installed to the PCB may be electrically connected to a main body control unit embedded in the main body, and the cartridge control unit may transmit the position data of the piezoelectric motor and the skin contact data to the main body control unit.

In addition, in a cartridge for a HIFU skin care device according to a preferred embodiment of the present invention, when the cartridge is mounted to the main body, the cartridge control unit installed to the PCB may be electrically connected to a main body control unit embedded in the main body, and the main body control unit may control a motor driver and a HIFU driver which are required to drive the ultrasonic wave transducer.

In addition, according to a fifth aspect of the present invention, a HIFU skin care unit has the cartridge for a HIFU skin care device.

ADVANTAGEOUS EFFECTS

According to the present invention, a HIFU apparatus can be used as a portable apparatus and has an effect of being capable of lifting the skin at any time and place. Users may use a beauty instrument for personal use and therefore conveniently manage the skin while treating skin wrinkles.

In addition, the HIFU apparatus may of course be used also in a hospital and a dedicated skin care shop.

In addition, a mechanical mechanism regarding the driving of a transducer is completed, not outside (inside the main body) a cartridge but inside the cartridge (outside the main body) of the portable HIFU skin care device, and thus, the performance of the portable HIFU skin care device may be maintained or improved by replacing the cartridge even when replacing the cartridge several times.

In addition, even though an effect is not specifically described herein, the effect described in the description below and expected by the technical feature of the present invention and a temporary effect thereof will be considered as being described in the specification of the present invention.

It is clarified that the attached drawings are illustrated as a reference for understanding the technical concept of the present invention, and the scope of the present invention is not limited by the drawings.

MODE FOR CARRYING OUT THE INVENTION

Hereinafter with reference to drawings, the configuration of the present invention introduced by various embodiments of the present invention, and the effect caused by the configuration will be described. In describing the present invention, detailed descriptions related to well-known functions and matters obvious to a person skilled in the art will be ruled out when the functions and matters unnecessarily obscures the subject matters of the present invention.

Figure 1:
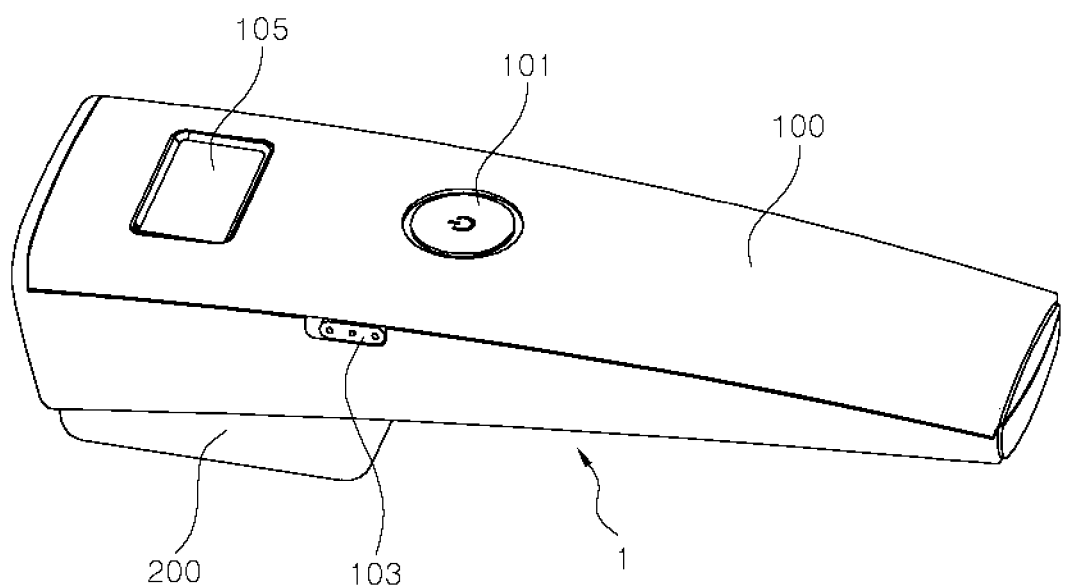
FIG. 1 illustrates an external configuration of a portable HIFU skin care device 1 according to a preferred embodiment of the present invention.

FIG. 1 illustrates an external configuration of a portable HIFU skin care device 1 according to a preferred embodiment of the present invention. The main body 100 and the cartridge 200 are in a state of being coupled to each other in FIG. 1. FIG. 1 illustrates an embodiment in which a portable device is used by charging an internal battery, but a cartridge for a skin care device of the present invention may not necessarily be understood limitedly to be used only in a portable main body. In addition, a cartridge for a skin care device, as long as being implemented by the function/configuration/structure disclosed in claims, may be used by being attached/detached to/from a main body having various physical/electronic configurations. For example, a hand piece used by being connected to a commercial power supply may serve as the main body. It is to be considered that the shapes illustrated in the description and the configurations described below relate to respective preferred embodiments. Regarding at least a cartridge for a skin care device, in order to describe the principle and the configuration of the cartridge, an embodiment of a main body is required because the configuration of the main body should be described together.

As illustrated, an exterior of the main body 100 in which a controller is installed has a physical structure convenient to be held and used by the hand of a user. Preferably, the length may be 200-250 mm, the width may be 60-80 mm, and the thickness may be 50-80 mm in a state in which the cartridge 200 is mounted. The case is composed of a plastic material such as ABS or PC and silicon may be used for a sealing member.

A power button 101 is provided on a surface of the main body 100. A display 105 is installed on the same surface as the surface on which the power button 101 is installed. In addition, a step button 103 for adjusting steps of the intensity of an ultrasonic wave to be strong/intermediate/weak is installed on a side surface.

When pressing the power button 101 for at least 0.5 second, the display 105 is turned on with a buzzer sound. Various states of the portable HIFU skin care device 1 of the present invention may be displayed on the display 105 by means of numerals/characters/symbols/icons/pictures or the like.

The functions and operations of the present invention can be understood by describing the indication displayed on the display 105 according to the operations of the power button 101 and the step button 103 and the state of a battery. Accordingly, this will be exemplarily described in detail.

As described above, when pressing the power button 101 for at least 0.5 second, the device is booted and a state display is turned on through the display 105 with a buzzer sound. Preferably, the turn-on of the state display during power ON is to display a number of shots that can be used by a user.

In the present invention, 1 shot means an ultrasonic wave emission event in which a motor mounted to the cartridge 200 moves a distance of 10 mm with a period of 1 mm interval during the emission operation of the ultrasonic wave and returns again to an origin point, and the "number of shots" means the number of events in which such the high-intensity ultrasonic wave has been emitted. In a power ON state, when pressing the power button 101 for at least several seconds (for example, 3 seconds), the power is turned off while the display is changed into a state of displaying power OFF together with a buzzer sound.

When the battery inside the main body 100 is discharged, a battery icon of the display 105 is displayed so as to indicate the discharge, and warns a user of charging while outputting a buzzer sound at intervals of several seconds. When an adaptor is connected to an input end of a charging cradle after the main body 100 is placed on the charging cradle (300 of FIG. 2), the display 105 is turned on so as to indicate an in-charge state.

A use method for a user in an operation mode will be described below. After gripping the main body 100 of FIG. 1, the head portion of the cartridge 200 is brought into complete contact with an object to be treated. Subsequently, when the power button 101 is shortly pressed once, a shot icon is displayer and turned on with a buzzer sound, an ultrasonic wave is emitted with driving of the motor, and then the number of uses is displayed on a display window by numerals. In this operation mode, the user may adjust in advance the intensity of the ultrasonic wave to be strong/intermediate/weak using the step button 103. This intensity of the ultrasonic wave may be displayed by an icon through the display 105.

When reaching a replacement period of the cartridge 200, the character "CHANGE" is displayed and lighted on the display 105, and informs the user of the replacement of the cartridge. In a preferred embodiment, the maximum number of times of using the cartridge of the present invention is 10,000 shots. The maximum number of times may also be increased or decreased.

Figure 2:
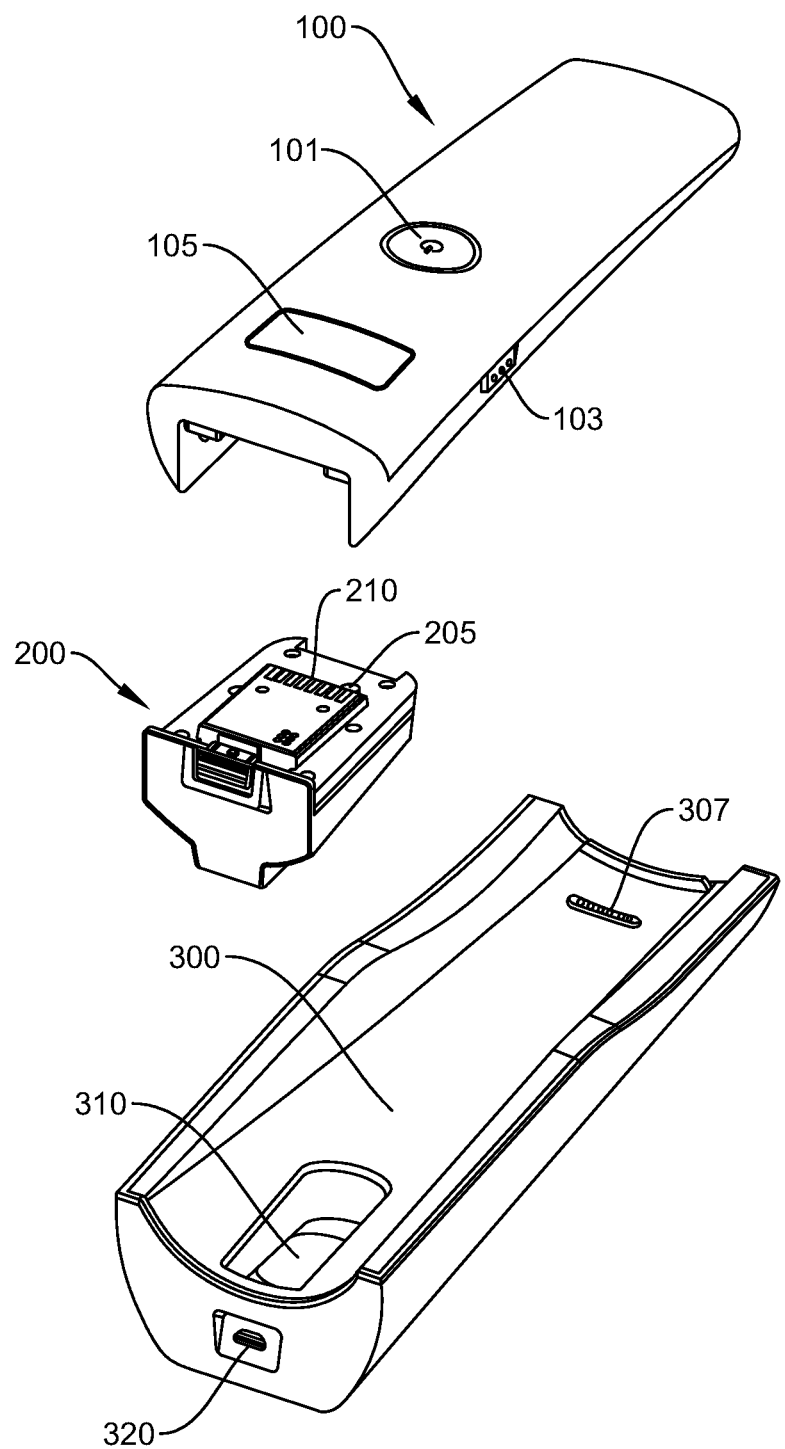
FIG. 2 is a view illustrating the portable HIFU skin care device 1 of FIG. 1 together with a cradle 300 in a state in which a main body 100 and a cartridge 200 are separated.

FIG. 2 illustrates an exploded configuration of a HIFU skin care device 1 including a cradle 300.

As illustrated, a cartridge 200 embedded with a HIFU transducer is attached/detached to/from an accommodation part under a head part of a main body 100. When the cartridge 200 is insertedly attached to the main body head accommodation section, a connector terminal part 210 forms an electrical contact with a main body connector part of the main body. The cartridge 200 stores distilled water functioning as a medium during emission of a high-intensity focused ultrasonic wave, and the distilled water also serves the function of cooling an overheating phenomenon that may occur. Therefore, a distilled water introducing port 205 is installed in a surface of the cartridge 200 and is connected to an internal sealed distilled-water tank (not shown).

A charging part 320 capable of charging by being connected with an adaptor is installed to the cradle 300. The charging part 320 may favorably be configured by a micro 5-pin USB charge connector. While being attached to the head of the main body 100, the cartridge 200 may be coupled to the cradle 300 in order to charge and place the portable HIFU skin care device. The head of the cartridge 200 is inserted into a placement groove 310 of the cradle 300. Then, while a UV lamp (not shown) embedded in the placement groove 310 turns on, the head part of the cartridge 200 is disinfected with UV, and a battery inside the main body 100 is charged via a cradle charging terminal 307 (the cradle charging terminal 307 is electrically connected to a main body charging terminal 107 of FIG. 3). At this point, a charging state is displayed through the display 105 of the main body 100.

Unless the cradle 300 and the main body 100 are separated from the state of being coupled to each other, the portable HIFU skin care device 1 does not operate.

Figure 3:
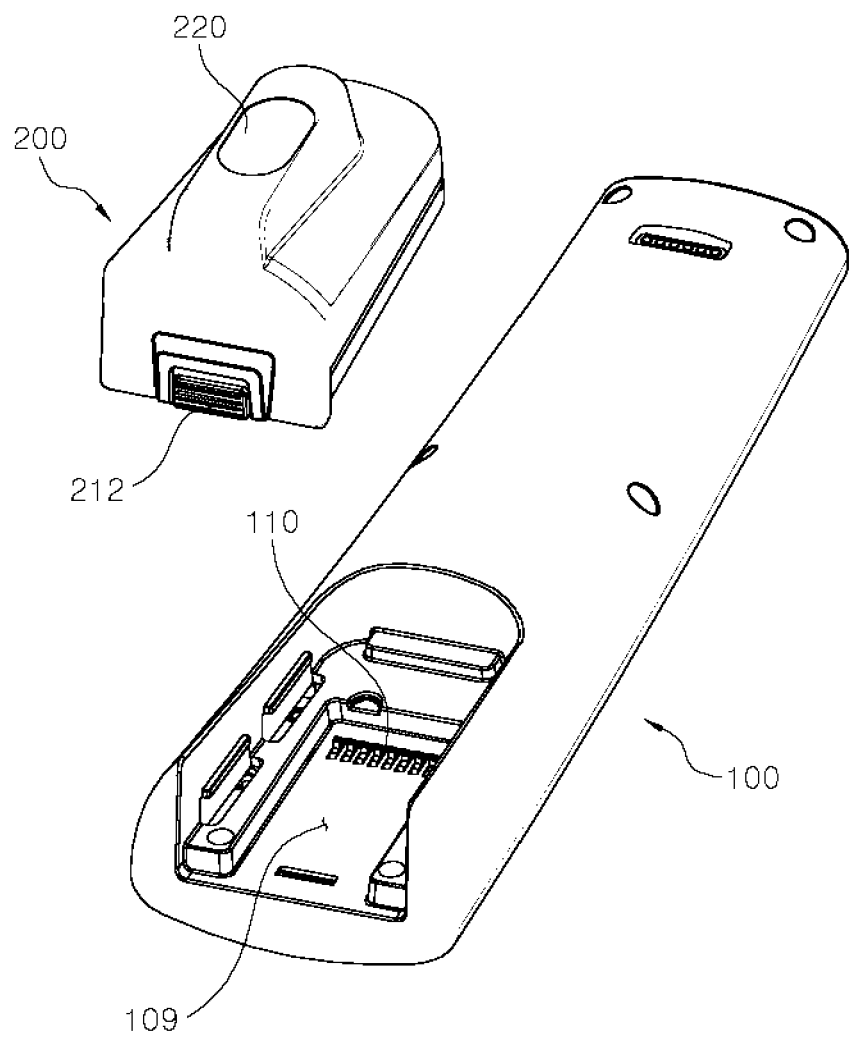
FIG. 3 is a view illustrating the main body 100 and the cartridge 200 in the reverse direction from FIG. 2.

FIG. 3 is a view for illustrating the main body 100 and the cartridge 200 in the reverse direction from of FIG. 2. The cartridge 200 is mounted through an opening of the head accommodation part 109 of the main body 100. Then, the cartridge connector terminal part 210 shown in FIG. 2 and the connector terminal part 110 of the main body form an electrical contact, and a control unit of the main body may thereby control an internal module of the cartridge.

A high-intensity focused ultrasonic wave emitted from the cartridge 200 is transmitted to an object via a cartridge window 220 of an action part.

Meanwhile, a user may press a cartridge replacement button 212 to detach the cartridge 200 from the main body 100.

Figure 4:
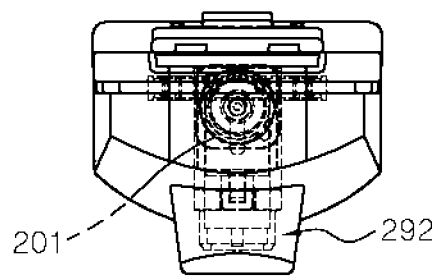
FIG. 4 is a view of the configuration of a cartridge 200 according a preferred embodiment of the invention from various angles.
Figure 4:
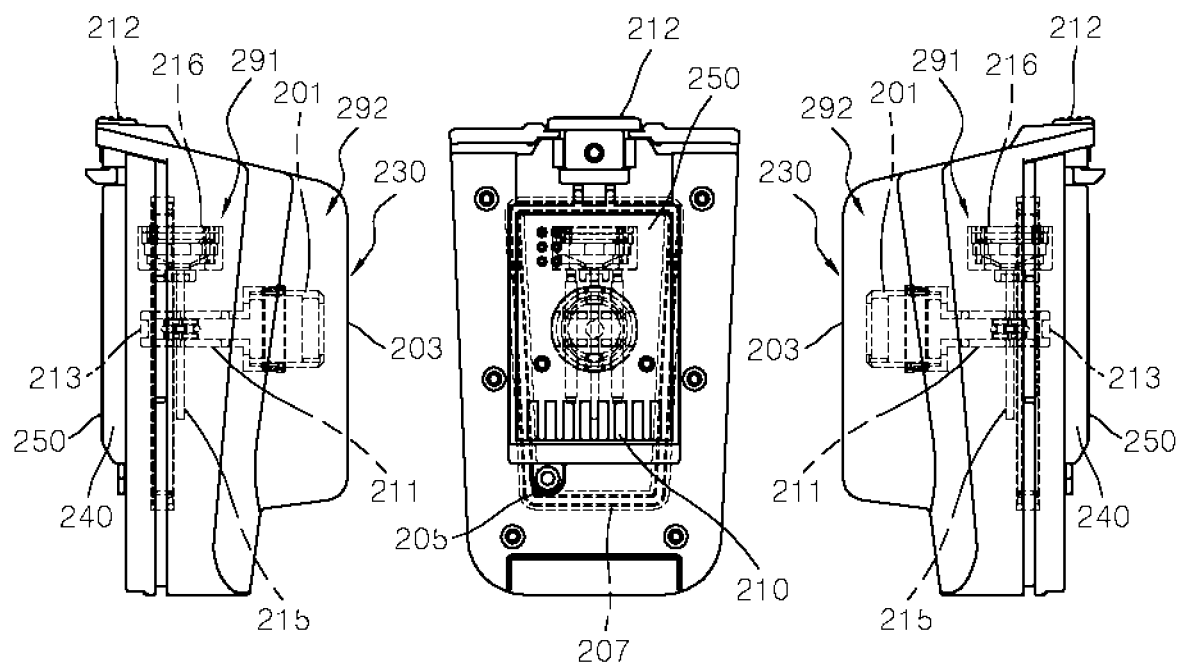
Figure 4:
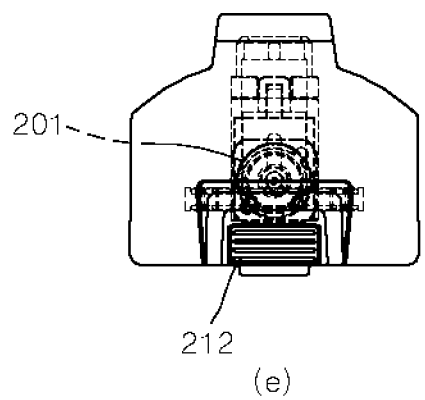

FIG. 4 illustrates a configuration of the cartridge 200 in a preferred embodiment of the present invention in three dimensions in five directions. FIG. 4C illustrates the rear surface.

A control unit including internal electronic elements (not shown) is installed to a PCB 250 of the cartridge 200, and a connector terminal part 210 is exposed to the outside. The PCB is installed on a rear surface protrusion part 240 on the exterior of the housing of the cartridge 200. The rear surface protrusion part 240 are formed to protrude from the rear external surface of the cartridge 200, and an accommodation groove (not shown) is provided by the thickness so that the PCB 250 is inserted into the groove. In addition, the PCB 250 is mounted to the accommodation groove in the rear surface protrusion part 240. In addition, a cable electrically connected to the PCB 250 is connected to a transducer moving mechanism device located inside the housing.

Two chambers are provided in the reverse side of the rear surface of the cartridge 200. A first chamber 291 and a second chamber 292 communicate with each other and function as tanks for storing distilled water. The transducer moving mechanism device including a piezoelectric motor 216 is installed in the first chamber 291. The transducer moving mechanism device includes a mover and a mover module that will be described later.

While an exterior front surface of the housing serves as an action part, the second chamber 292 protrudes frontward in a smaller width than the first chamber 291. The exterior protruding surface serves as the action part and comes into contact with an object. The housing of the HIFU transducer is located inside the second chamber 292.

A sealing member 207 for sealing so as to prevent the distilled water stored in the chambers 291 and 292 from leaking to the outside is inserted into an entrance, corresponding to the rear surface protrusion part, of the first chamber 291.

Figure 5:
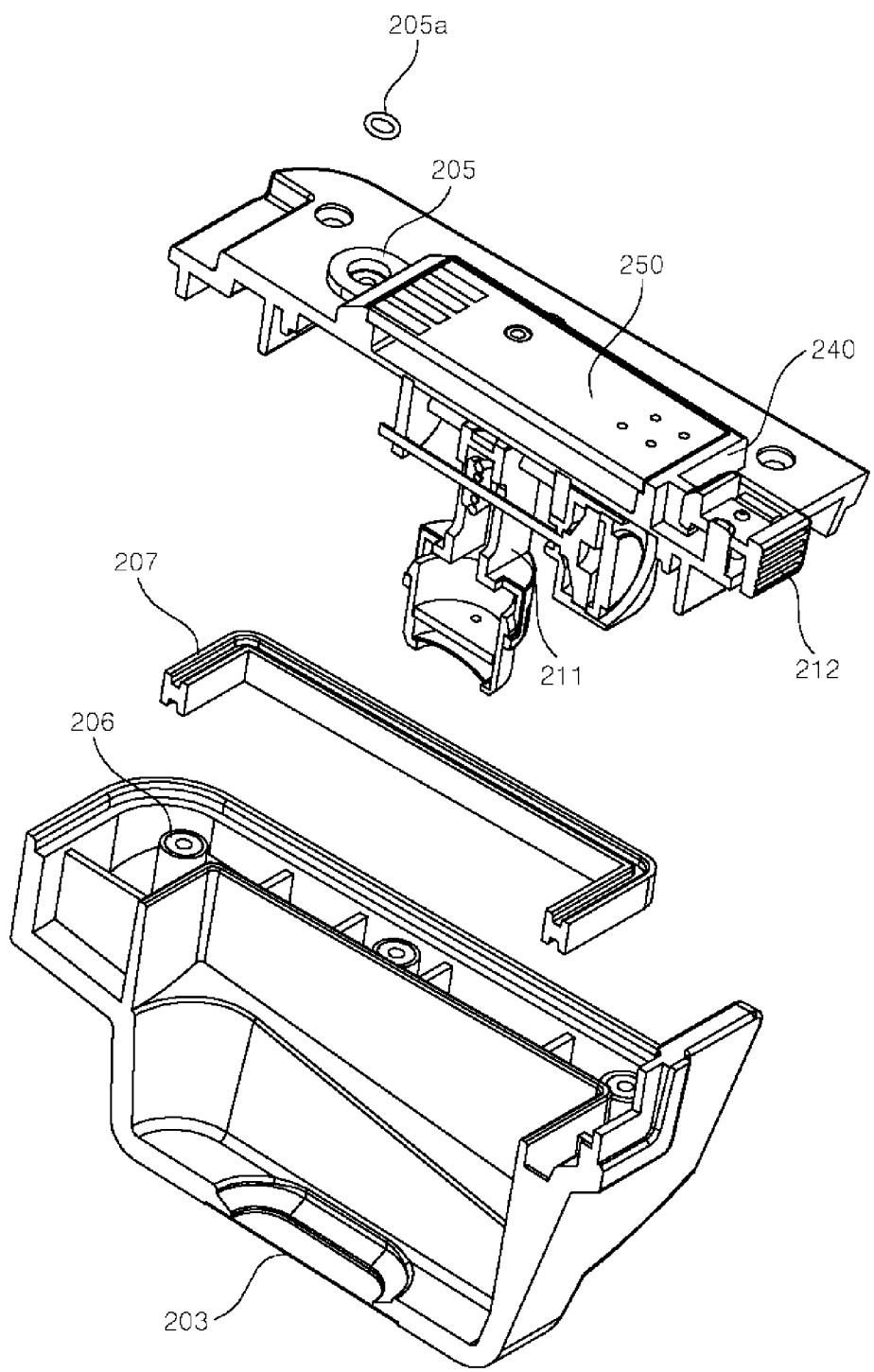
FIGS. 5 and 6 are views illustrating cross-sections of FIG. 4.
Figure 6:
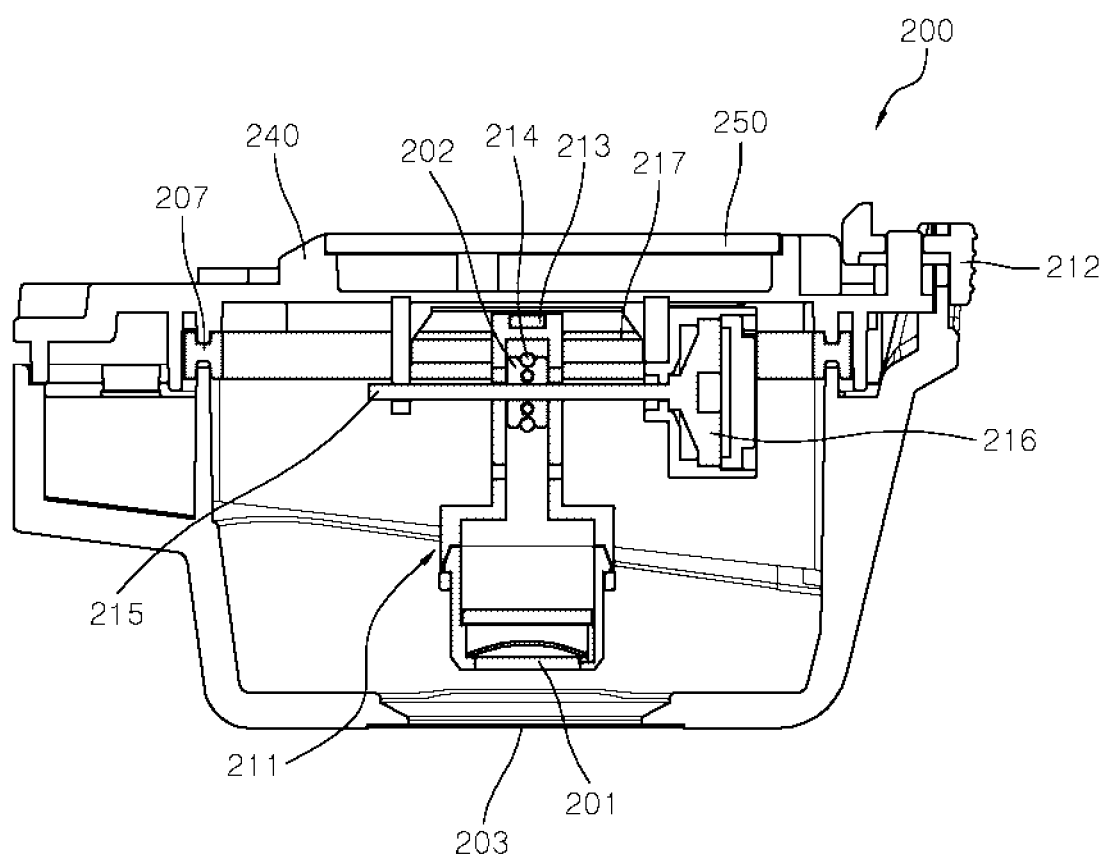

FIG. 5 is an exploded perspective view illustrating a central portion of the cartridge 200 of FIG. 4 after cutting the cartridge in the direction from the rear surface to the front surface, and FIG. 6 is a cross-sectional view in which the exploded perspective views of FIG. 5 are assembled.

With reference to FIGS. 5 and 6, the internal configuration of a cartridge 200, and the installation method and the location of the sealing member 207 may be easily understood. In addition, the configurations of the rear surface protrusion part 204 and the PCB 250 may be correctly understood.

Even a small hole is sufficient as a distilled water introduction port 205 because the introduction of distilled water is favorably performed by using a syringe, and more specifically, a nut is installed which may be opened/closed by using a bolt having a diameter of approximately 1-3 mm. In addition, a waterproof rubber 205*a* may favorably be inserted into the distilled water introduction port 205.

In addition, six fastening nuts 206 may favorably be installed to couple the rear surface housing to the front surface housing (in FIG. 5, only three fastening nuts 206 are seen because only the half of the housing of the cartridge 200 is illustrated).

The ultrasonic wave transducer 201 is coupled to a mover module 211. Accordingly, the position of the ultrasonic wave transducer 201 is changed accompanying the movement of the mover module 211. In an upper end of the mover module 211, a mover 202 is installed to a carbon shaft connected to a piezoelectric motor 216 by means of a mover fixation rubber 214 and a mover module fixation part 217. A mover detection sensor 213 detects the position of the mover.

When the piezoelectric motor 216 is driven, the mover 202 displaces to a predetermined position, and thus, the position of the ultrasonic wave transducer 201 is determined. Meanwhile, a high-intensity ultrasonic wave emitted toward an object from the ultrasonic wave transducer 201 passes through a window 203 installed at the central section of the action part, and an ultrasonic wave permeable film, such as a polyimide or polyethylene film may be used for the window 203.

Figure 7:
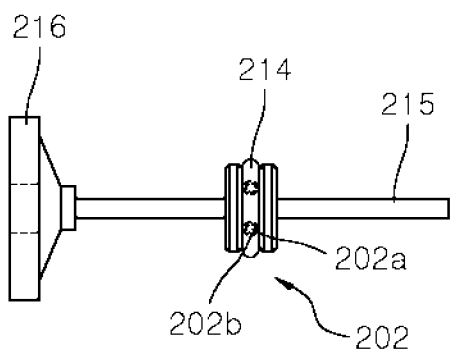
FIG. 7 is a view exemplarily illustrating the relationship between a piezoelectric motor 216 and a mover 202 according to a preferred embodiment of the present invention.
Figure 7:
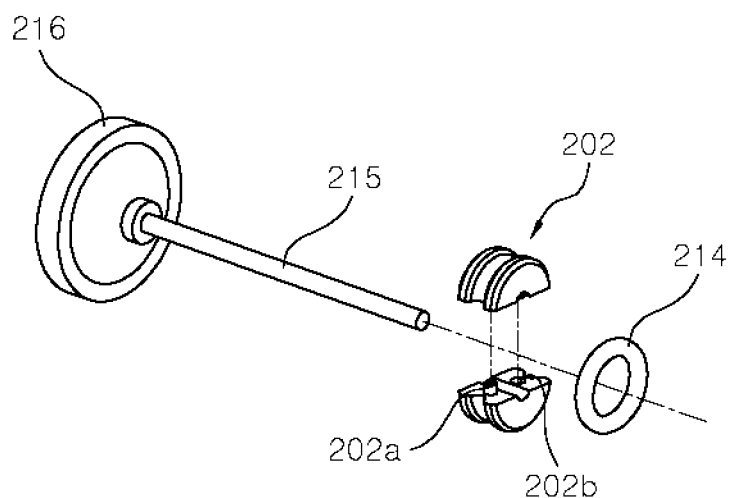
Figure 7:
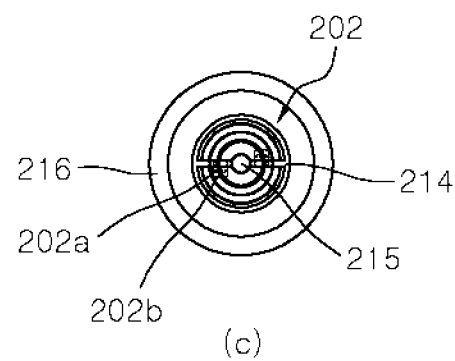

FIG. 7 is a view exemplarily illustrating the relationship between a piezoelectric motor 216 and a mover 202 according to a preferred embodiment of the present invention. FIG. 7A illustrates a state in which the mover 202 is installed to a carbon shaft 215 having one end to which the piezoelectric motor 216 is installed, FIG. 7B illustrates a state in which members are separated to help understanding the configuration of the internal configuration of the mover 202, and FIG. 7C illustrates a planar configuration of the mover 202 in a state in which the members are coupled.

In an embodiment of the present invention, a structure is provided such that the carbon shaft 215, which linearly transmits, to the mover 202, the displacement generated by the piezoelectric motor 216, passes through the center of the mover 202. That is, the center of the mover 202 is formed as a hole through which the carbon shaft 215 passes. The body of the mover 202 may be divided into two pieces as illustrated and be inserted into each other and installed to the carbon shaft 215.

Each of a pair of mover pieces is provided with a protruding fixation guide 202a and a recessed fixation hole 202b. The mover fixation guide 202a of a first mover piece is inserted into the mover fixation hole 202b of a second mover piece. Likewise, the mover fixation guide 202a of the second mover piece is inserted into the mover fixation hole 202b of the first mover piece, so that the single mover 202 is configured by the coupling of the pieces of the mover. At this point, a recess part is provided in the body of each piece of the mover so that a circular recess part having a semi-circular cross-section may be formed in the central portion between the front and rear ends of the mover. In addition, the mover fixation rubber 214 is inserted into the recess part, so that integrated coupling of the mover 202 is completed.

By using the abovementioned configuration, a mechanism for linearly moving the ultrasonic wave transducer 201 inside the cartridge 200 is completed.

Figure 8:
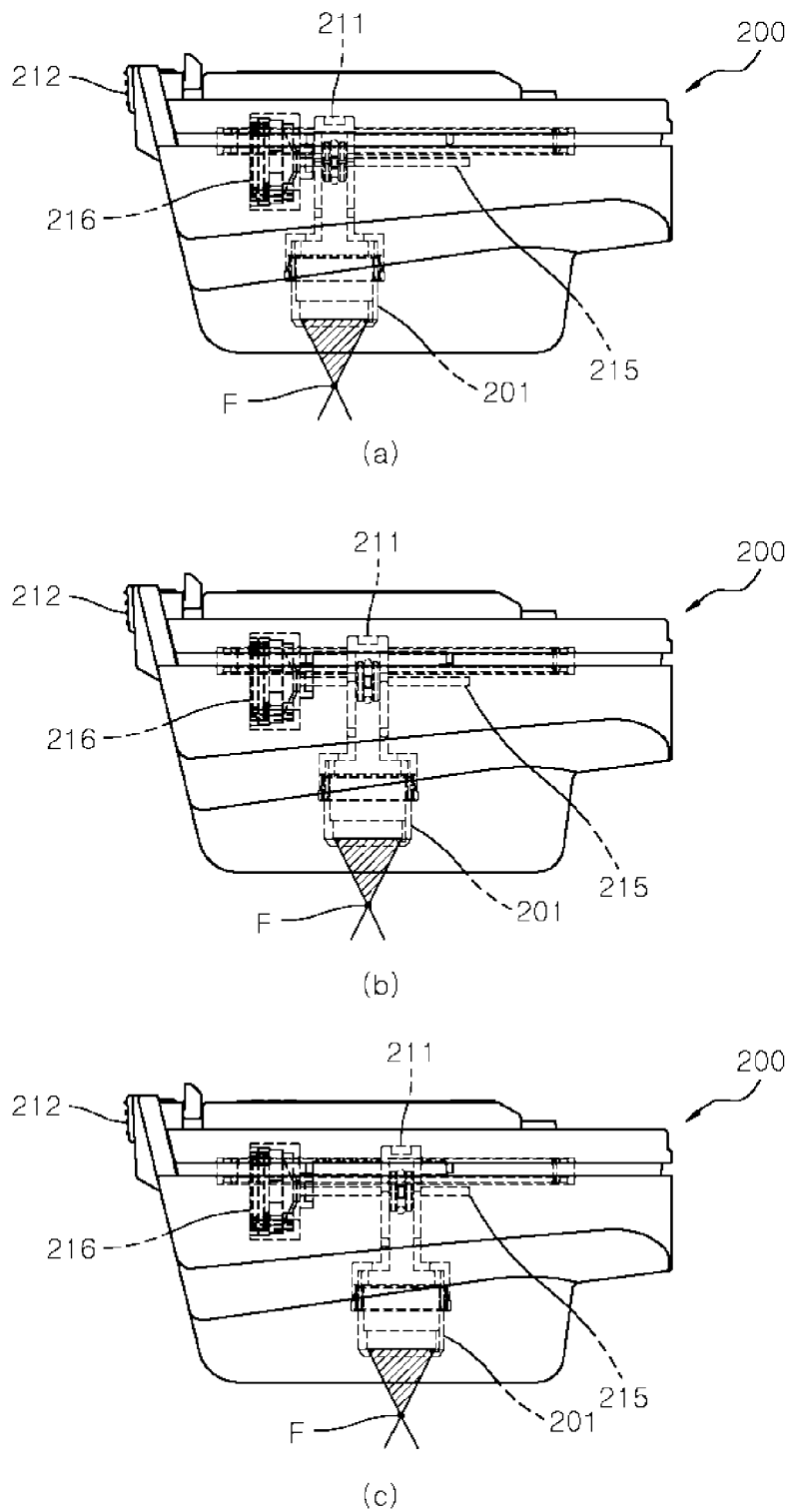
FIG. 8 is a view illustrating a principle of a linear operation of an ultrasonic wave transducer 201 of a cartridge 200 according to a preferred embodiment of the present invention.

Referring to FIG. 8, when an ultrasonic wave transducer 201 starts operation, the transducer is linearly moved from an initial position of FIG. 8A to the positions of FIGS. 8B and 8C. When a piezoelectric motor 216 operates, the ultrasonic wave transducer 201 moves 1 mm via a carbon shaft 215. Then, the position of an ultrasonic wave focal point F created by the ultrasonic transducer 201 is also changed, so that an ultrasonic wave focal point region formed on an object is also changed. As such, a skin care effect is achieved by emitting a high-intensity focused ultrasonic wave and changing the position of the ultrasonic wave focal point F.

Figure 9:
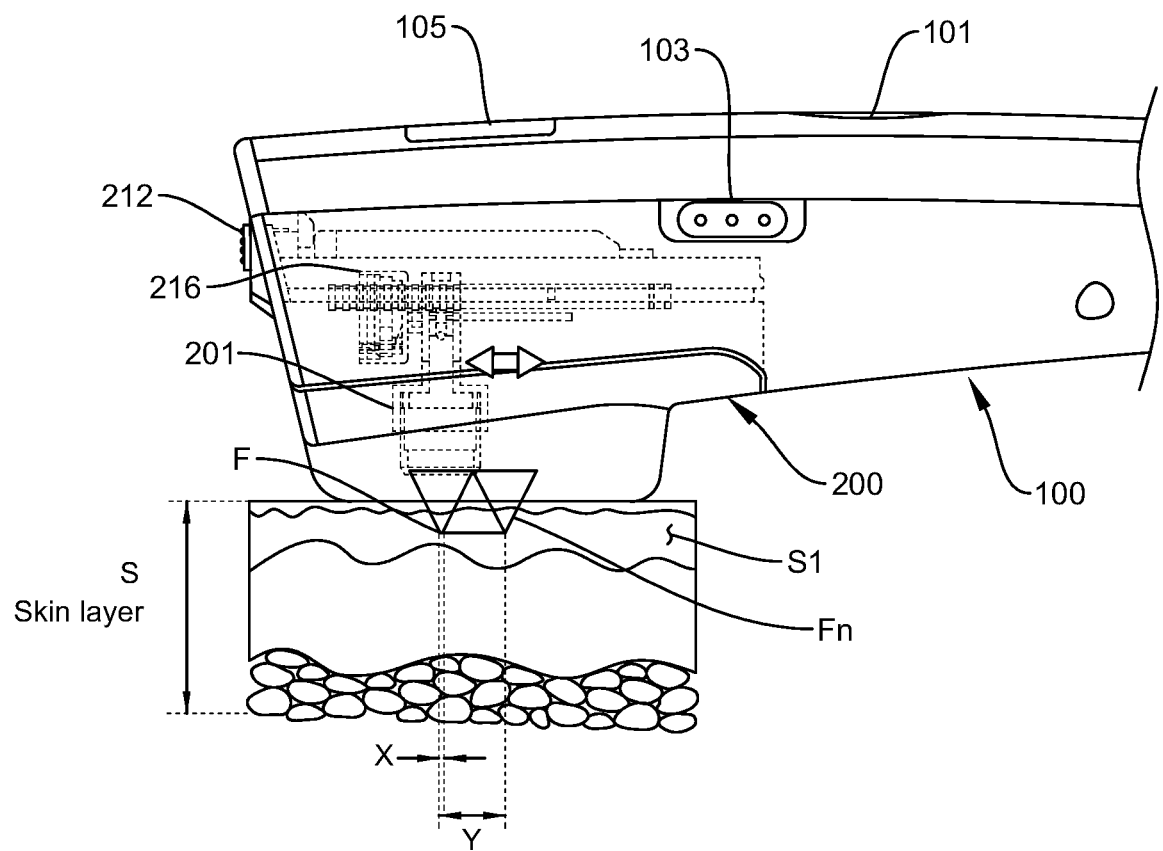
FIG. 9 is a view exemplarily illustrating an operation principle for achieving skin care of a portable HIFU skin care device of the present invention.

As shown in FIG. 9, a focal point F, to which the high-intensity ultrasonic wave emitted through the ultrasonic transducer 201 is focused, forms the focal point only in an ultrasonic focal point region S1 in a skin layer S of an object. The present invention may be configured such that the ultrasonic wave is emitted the total of ten times particularly during one shot. Every time the ultrasonic wave is emitted once for each 1 mm, movement of 1 mm is implemented by driving the motor, and thus, a focal point region of 10 mm is formed during one shot.

That is, the high-intensity ultrasonic wave is applied only to a kin tissue in the ultrasonic focal point region S1 and a wound is generated due to heat of, for example, 65-100° C. As such, a stimulus is imparted to a skin tissue and a human body naturally responds to the stimulus, so that not only wrinkle treatment but also improvement in skin elasticity may be achieved. Due to the principle of focusing of high-intensity ultrasonic wave, no wound remains on the surface of the object contacting a window of the ultrasonic wave transducer 201.

Figure 10:
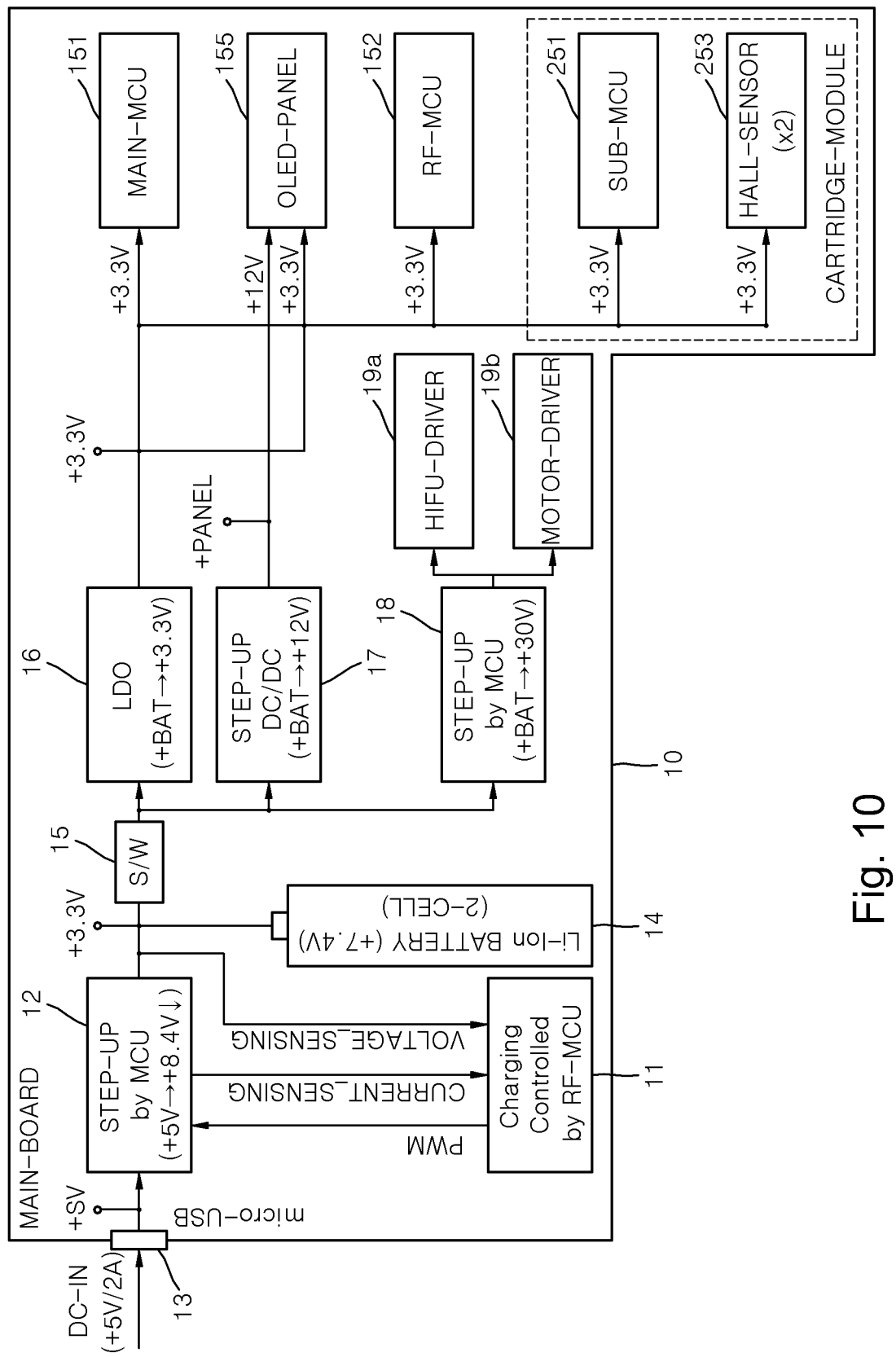
FIG. 10 illustrates an example of an electronic configuration of a portable HIFU skin care device according to a preferred embodiment of the present invention.

FIG. 10 exemplarily illustrates a block diagram of a power line in an electronic configuration embedded in a portable HIFU skin care device according to a preferred embodiment of the present invention.

Three types of MCUs 151, 152 and 251 are used in a portable HIFU skin care device equipped with a cartridge of the present invention.

The 5V/2A DC power input to a device main board through a USB connector 13 is stepped up into charging power by means of a first MCU 151, and charges a battery 14 while receiving charging control of a second MCU 152. A chargeable lithium ion battery having a specification of DC 7.4 V/2500 mAh is used as the battery 14 of the present invention. Two batteries are favorably used by being connected to each other.

As described above, while a main body is placed and charged on a cradle, the device of the present invention does not operate. The power of the battery 14 is supplied to each of electronic elements by detaching the main body from the cradle and turning on a switch 15.

The power of the battery 14 is distributed into three branches and supplied to the electronic elements. The power is supplied as system power for the MCUs 151, 152, and 251, a sensor 253, and an OLED panel 155 at DC power of 3.3 V via a low drop output regulator (LDO) 16, and is raised to 12 V by a DC/DC converter 17 and is supplied as power for performing a state display function of the OLED panel 155. In addition, the battery voltage is raised to 30 V as the driving power of a HIFU driver 19a and a motor driver 19b and is supplied to each of the drivers 19a and 19b.

Configurations separable into a cartridge module 20 are connected to the main body, so that the voltage of the battery 14 in the main body may be used. When the cartridge module is detached from the main body, the power supply to the cartridge module 20 is disconnected.

Figure 12:
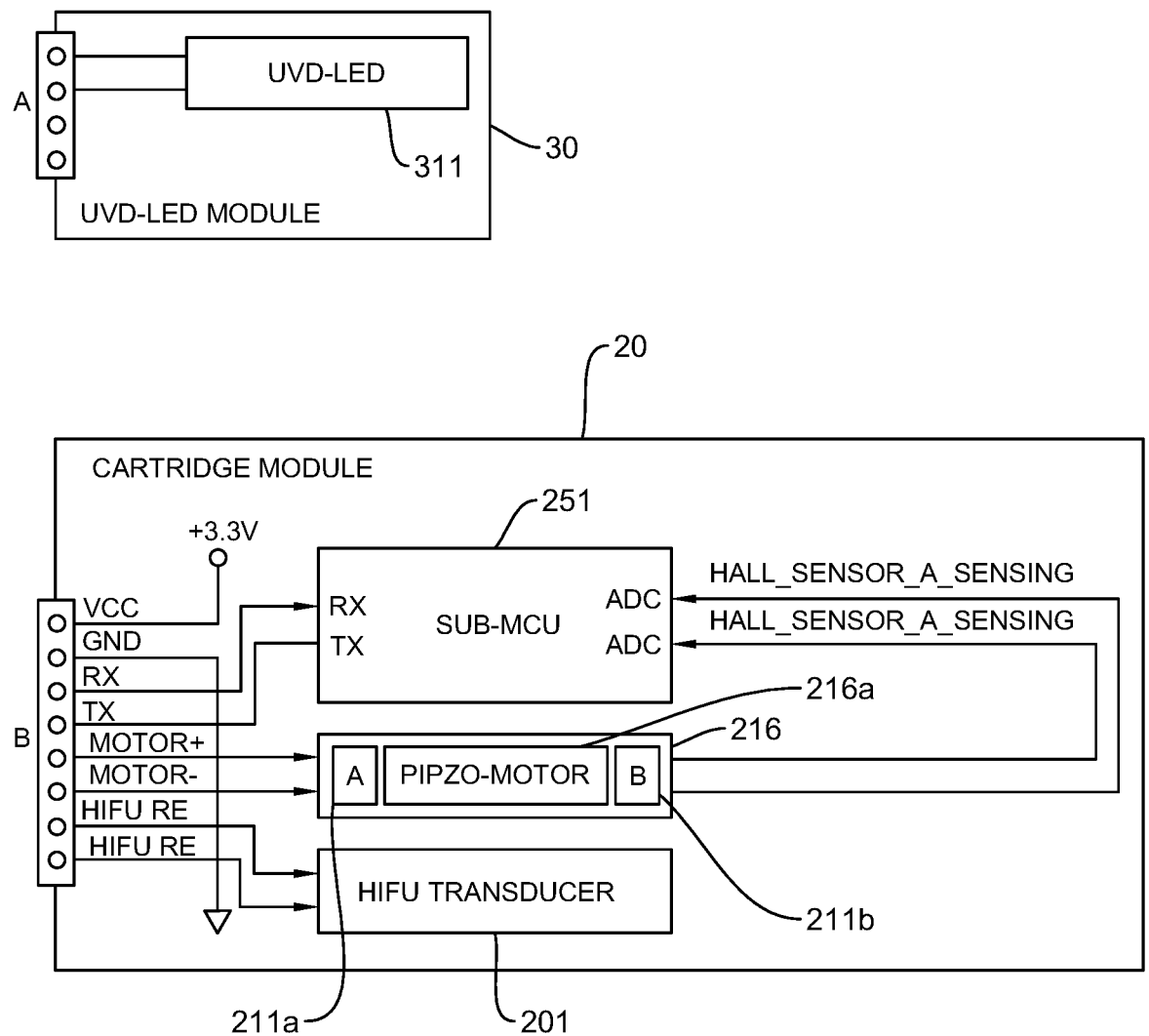
FIG. 12 is a block diagram illustrating examples of internal configurations of a cradle LED module 30 and a cartridge module 20 of a portable HIFU skin care device according to a preferred embodiment of the present invention.

The relationship between and the functions of the abovementioned three types of MCUs will be described below. FIGS. 10 and 12 illustrate configurations of preferred embodiments. The first MCU 151 and the second MCU 152 constitute a main body control unit, and the third MCU 251 constitutes a cartridge control unit.

The first MCU 151 controls the functions of an input/output device of the portable HIFU device of the present invention, and controls the operations of the cartridge module 20 and a UVC-LED 311 of a cradle LED module 30.

The first MCU 151 transmits a control signal to a UVC_LED driver 161, a regulator 163 for supplying system power ON/OFF, an OLED panel 155, a buzzer 157 and the cartridge module 20. In addition, the first MCU receives a signal from a power switch 199, a power detection unit 192a of an adaptor, and a side surface switch 193. In addition, an ADC terminal of the first MCU 151 receives a voltage from a battery terminal 154. In addition, a firmware is downloaded through an ISP terminal 181.

The second MCU 152 communicating with the first MCU 151 controls the HIFU driver 19a and the motor driver 19b which are required for correct operations of a piezoelectric motor 216a of the cartridge module 20 and the HIFU transducer 201.

The second MCU 152 transmits a motor control signal to the motor driver 19b, and transmits an RF pulse signal to the HIFU driver 19a. In addition, the second MCU 152 detects (192b) input power and receives the signal of the input power, and PWM terminals transmit PWM control signals to a voltage raising module 18, and transmits the PWM control signals to a charging voltage raising module 12. The ADC terminals receive current and voltage feedbacks.

In addition, the second MCU 152 receives temperature data via an NTC thermistor 170. In addition, a firmware is downloaded through an ISP terminal 182.

Figure 11:
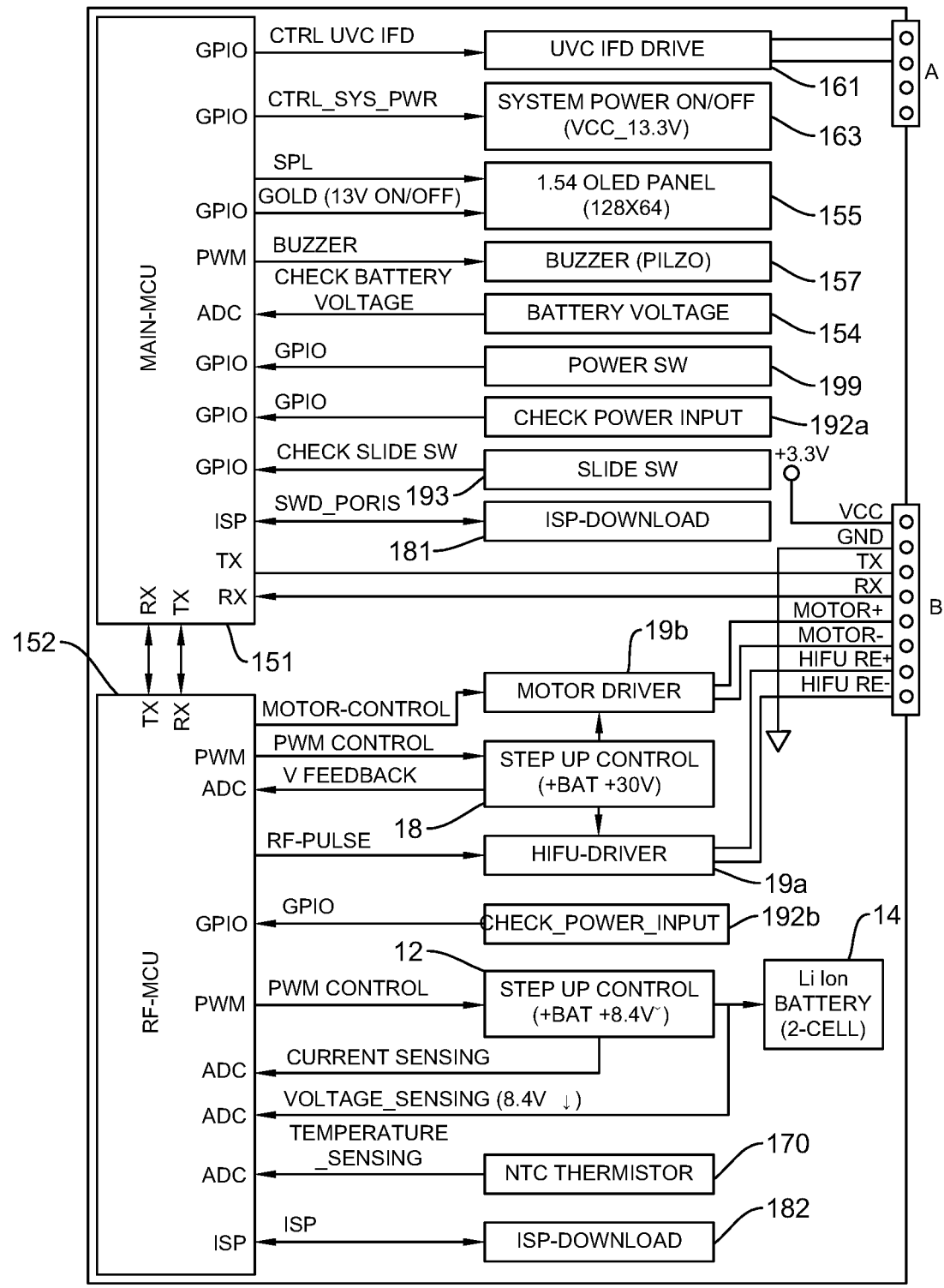
FIG. 11 is a block diagram illustrating functions of a first MCU 151 and a second MCU 152 of a portable HIFU skin care device according to a preferred embodiment of the present invention.

In addition, a firmware is downloaded through the ISP terminal (182). The portions depicted as connectors A and B of FIG. 11 are shown as A and B of FIG. 12. That is, the first MCU is connected to the cradle LED module 30 via the connector A. In addition, the first MCU 151 and the second MCU 152 are connected to the cartridge module 20 via the connector B and communicate with the third MCU 251.

The third MCU 251 provided to the cartridge module 20 receives movement data about the motor 216a via a first Hall sensor 211a and receives skin contact data via a second Hall sensor 211b. In addition, the third MCU transmits, to the first MCU 151, data received from the cartridge module 20, and receives a control signal. Meanwhile, the HIFU transducer 201 and the motor 216a provided to the cartridge module 20 respectively receive control signals from the HIFU driver 19a and the motor driver 19b of the second MCU 152.

In the portable HIFU skin care device of the present invention, the first MCU 151 serves the functions and roles of a first control unit, the second MCU 152 serves the functions and roles of a second control unit, and the third MCU 251 serves the functions and roles of a third control unit. On the basis of the above descriptions, each of the control units will be further described repeatedly in terms of constituent element.

In a preferred embodiment of the present invention, the first control unit may include a UART communication handler processing unit, a time handler processing unit, an OLED panel drive control unit, a piezoelectric buzzer drive control unit, a UVC LED drive control unit, a user key processing unit, a battery voltage detection unit, and an input voltage detection unit.

The UART communication handler processing unit serves a control function for setting an output intensity in response to a communication command with the second MCU 152. In other words, the operation of the UART communication handler processing unit is to set ultrasonic outputs of step 1 (strong), step 2 (intermediate), and step 3 (weak). In addition, the UART communication handler processing unit performs the following operations in response to a communication command with the third MCU 251.

Request the total number of shots to the third MCU 251
Transmit the number of times of use and request storage thereof
Receive the position data of the piezoelectric motor from the third MCU 251
Receive skin contact presence/absence data from the third MCU 251

The time handler processing unit automatically turns off power when a preset time elapses, and serves a timer function pertaining to time such as a UVC LED operation time.

The OLED panel drive control unit serves a control function for displaying user's function selection and operation states via the display.

The piezoelectric buzzer drive control unit allows a preset buzzer sound to be output.

The UVC LED drive control unit drives a UVC LED 311 so that when the main body 100, to which the cartridge 200 is attached, is docked to the cradle 300, electrodes and touch sensor portion of a cartridge head contacting the skin may be disinfected and sterilized.

The user key processing unit receives user's key input signal and processes function control.

The battery voltage detection unit detects the battery voltage and processes the voltage so that a battery charging state icon is displayed through the display, and the input voltage detection unit determines whether the main body is docked to the cradle.

In a preferred embodiment of the present invention, the second control unit may include a UART communication handler processing unit, a HIFU transducer drive control unit, a motor drive control unit, a battery charge control unit, and a system temperature detection unit.

In a preferred embodiment of the present invention, the third control unit may include a UART communication handler unit, a motor movement detection unit, and a skin contact presence detection unit. The UART communication handler processing unit executes the following operation in response to a communication command with the first MCU 151.

Transmit the total number of times of shots to the first MCU
Receive and store the use times
Transmit motor position data to the first MCU
Transmit skin contact presence/absence data to the first MCU The scope of the present invention is not limited by the examples and descriptions specifically described so far. Furthermore, it is stated once more that the scope of the present invention should not be construed to be limited by an obvious change or a substitution in the field to which the present invention pertains.

The invention claimed is:

1. A portable HIFU skin care device comprising:
    a main body (100) having a rechargeable battery embedded therein, a power button and a step button for adjusting the intensity of an ultrasonic wave, the buttons being installed therein, and a display for displaying operation states of the device, including the number of shots;
    a cartridge (200) used by being mounted on a head part of the main body (100) and having a HIFU transducer embedded therein; and
    a cradle (300) comprising a charging part installed therein and capable of charging by being connected with an adaptor, configured to accommodate the main body (100) via a placement groove while the cartridge (200)

is attached to the main body (100), comprising a UV lamp configured to disinfect the head portion of the cartridge (200) when the cradle accommodates the main body (100), and configured to charge an internal battery of the main body (100), wherein in an operation state, the HIFU transducer irradiates an object with a plurality of ultrasonic waves for each one shot while linearly moving by a piezoelectric motor installed inside the cartridge and thereby forms a plurality of ultrasonic wave focal point regions on the object.

2. The portable HIFU skin care device of claim 1, wherein the HIFU transducer moves 1 mm ten times during one shot and thereby forms a focal point region of 10 mm on the object.

3. A portable HIFU skin care device comprising:
a main body (100) having a rechargeable battery embedded therein, a power button and a step button installed therein for adjusting the intensity of an ultrasonic wave, and a display for displaying operation states of the device, including the number of shots;
a cartridge (200) used by being mounted on a head part of the main body (100) and having a HIFU transducer embedded therein; and
a cradle (300) comprising a charging part installed therein and capable of charging by being connected with an adaptor, and configured to accommodate the main body (100) via a placement groove and charge an internal battery of the main body (100) while the cartridge (200) is attached to the main body (100), wherein:
three control units are installed inside the portable HIFU skin care device;
a first control unit and a second control unit are installed inside the main body (100) and a third control unit is installed to the cartridge (200);
the first control unit, which is a main control unit, controls a function of an input/output device of the portable skin care device, receives position data and skin contact presence/absence data about the piezoelectric motor from the third control unit, and transmits the data to the second control unit;
the second control unit controls a motor driver and a HIFU driver which are required to drive the piezoelectric motor and the HIFU transducer that are installed inside the cartridge (200); and
the third control unit performs an operation of transmitting, to the first control unit, the number of shots made by driving the motor driver and the HIFU driver of the second control unit.

4. A portable HIFU skin care device comprising:
a main body (100) having a rechargeable battery embedded therein, a power button and a step button installed therein for adjusting the intensity of an ultrasonic wave, and a display for displaying operation states of the device, including the number of shots;
a cartridge (200) used by being mounted on a head part of the main body (100) and having a HIFU transducer embedded therein; and
a cradle (300) comprising a charging part installed therein and capable of charging by being connected with an adaptor, and configured to accommodate the main body (100) via a placement groove and charge an internal battery of the main body (100) while the cartridge (200) is attached to the main body (100), wherein:
a PCB in which a control unit for the cartridge (200) is installed is installed on a rear surface protrusion part on an exterior of a cartridge housing, and when the PCB is mounted on the main body (100), a connector terminal part of the PCB and a connector installed on the head part of the main body (100) are electrically connected to each other;
a transducer moving mechanism including a piezoelectric motor is installed in a first chamber inside the cartridge (200);
the housing of the HIFU transducer is positioned inside a second chamber, which protrudes toward a front surface in a smaller width than the first chamber while communicating with the first chamber; and
the protruding surface of the second chamber is configured as an action part brought into surface contact with the object.

5. The portable HIFU skin care device of claim 4, wherein the first chamber and the second chamber communicate with each other and function as tanks that accommodate distilled water.

6. The portable HIFU skin care device of claim 4, wherein a sealing member is further installed to an entrance corresponding to the rear surface protrusion part of the first chamber.

7. The portable HIFU skin care device of claim 4, wherein a window through which a high-intensity ultrasonic wave is emitted is installed in the middle of the action part.

8. A cartridge that is for a HIFU skin care device, is used by being mounted on the head part of the main body, and is separable from the main body, the cartridge comprising:
a PCB, in which a control unit for the cartridge is installed, is installed to a rear surface protrusion part on the exterior of a housing of the cartridge, and when the PCB is installed to the main body, a connection terminal of the PCB and a connector installed on the head part of the main body are electrically connected to each other;
an ultrasonic wave transducer moving mechanism device comprising a piezoelectric motor is installed in the first chamber inside the cartridge;
a housing of the ultrasonic wave transducer is positioned inside a second chamber communicating with the first chamber and protruding toward a front surface in a smaller width than the first chamber; and
an exterior protruding surface of the second chamber is configured as an action part brought into contact with an object.

9. The cartridge of claim 8, wherein:
the first chamber and the second chamber function as tanks which communicate with each other and stores distilled water; and
a sealing member is further installed to an entrance corresponding to the rear protruding part of the first chamber.

10. The cartridge of claim 8, wherein a window through which a high-intensity ultrasonic wave is emitted is installed in the middle of the action part.

11. The cartridge of claim 8, wherein:
the ultrasonic wave transducer moving mechanism device comprises a mover module coupled to the ultrasonic wave transducer;
a carbon shaft connected to the piezoelectric motor passes through a central hole of the mover installed to an upper end of the mover module;
a mover fixation hole and a mover fixation guide, which are installed to a pair of respective mover pieces divided into two pieces with respect to the central hole, are coupled to face each other; and the mover is installed to the carbon shaft by inserting a mover fixation rubber into a recess part of the mover.

12. The cartridge of claim 8, wherein:

when the cartridge is attached to the main body, a cartridge control unit installed to the PCB is electrically connected to a main body control unit embedded in the main body; and the cartridge control unit transmits position data of the piezoelectric motor and skin contact data to the main body control unit.

13. The cartridge of claim 8, wherein:

when the cartridge is attached to the main body, the cartridge control unit installed to the PCB is electrically connected to a main body control unit embedded in the main body; and the main body control unit controls a motor driver and a HIFU driver that are required to drive the ultrasonic wave transducer.

\* \* \* \* \*